US009346035B2

(12) United States Patent
Huber et al.

(10) Patent No.: US 9,346,035 B2
(45) Date of Patent: *May 24, 2016

(54) SUPPORTED NOBLE METAL-COMPRISING CATALYST FOR OXIDATIVE DEHYDROGENATION OR EPOXIDATION

(71) Applicant: BASF SE, Ludwigshafen (DE)

(72) Inventors: Sabine Huber, Bobeheim-Roxheim (DE); Tobias Rosendahl, Mannheim (DE); Georg Seeber, Lambsheim (DE); Christian Baltes, Lampertheim (DE)

(73) Assignee: BASF SE (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/418,487

(22) PCT Filed: Jul. 31, 2013

(86) PCT No.: PCT/EP2013/066063
§ 371 (c)(1),
(2) Date: Jan. 30, 2015

(87) PCT Pub. No.: WO2014/020054
PCT Pub. Date: Feb. 6, 2014

(65) Prior Publication Data
US 2015/0151278 A1    Jun. 4, 2015

Related U.S. Application Data

(60) Provisional application No. 61/678,143, filed on Aug. 1, 2012.

(30) Foreign Application Priority Data

Aug. 1, 2012  (EP) ..................... 12178872

(51) Int. Cl.
| | |
|---|---|
| C07C 45/00 | (2006.01) |
| B01J 23/00 | (2006.01) |
| B01J 37/00 | (2006.01) |
| B01J 23/50 | (2006.01) |
| B01J 37/02 | (2006.01) |
| B01J 37/08 | (2006.01) |
| B01J 37/16 | (2006.01) |
| B01J 23/30 | (2006.01) |
| B01J 23/42 | (2006.01) |
| B01J 23/44 | (2006.01) |
| B01J 23/46 | (2006.01) |
| B01J 23/52 | (2006.01) |
| B01J 23/72 | (2006.01) |
| C07C 45/38 | (2006.01) |
| B01J 23/38 | (2006.01) |
| C07C 45/29 | (2006.01) |
| C07C 45/39 | (2006.01) |
| B01J 23/02 | (2006.01) |
| B01J 35/00 | (2006.01) |

(52) U.S. Cl.
CPC *B01J 23/50* (2013.01); *B01J 23/02* (2013.01); *B01J 23/30* (2013.01); *B01J 23/38* (2013.01); *B01J 23/42* (2013.01); *B01J 23/44* (2013.01); *B01J 23/462* (2013.01); *B01J 23/466* (2013.01); *B01J 23/52* (2013.01); *B01J 23/72* (2013.01); *B01J 35/0006* (2013.01); *B01J 37/02* (2013.01); *B01J 37/0217* (2013.01); *B01J 37/0219* (2013.01); *B01J 37/0228* (2013.01); *B01J 37/08* (2013.01); *B01J 37/088* (2013.01); *B01J 37/16* (2013.01); *C07C 45/00* (2013.01); *C07C 45/002* (2013.01); *C07C 45/29* (2013.01); *C07C 45/38* (2013.01); *C07C 45/39* (2013.01)

(58) Field of Classification Search
CPC ......... C07C 45/29; B01J 37/008; B01J 37/08; B01J 37/16
USPC .......................................... 568/489; 502/243
See application file for complete search history.

(56) References Cited

U.S. PATENT DOCUMENTS

| | | | |
|---|---|---|---|
| 4,165,342 | A | 8/1979 | Dudeck et al. |
| 5,149,884 | A | 9/1992 | Brenner et al. |
| 5,734,068 | A | 3/1998 | Klopries et al. |
| 6,013,843 | A | 1/2000 | Aquila et al. |
| 6,383,273 | B1 | 5/2002 | Kepner et al. |
| 8,604,252 | B2 | 12/2013 | Seeber et al. |
| 8,779,212 | B2 | 7/2014 | Mäurer et al. |
| 2011/0015446 | A1 | 1/2011 | Mäurer et al. |
| 2012/0108831 | A1 | 5/2012 | Seeber et al. |

FOREIGN PATENT DOCUMENTS

| | | |
|---|---|---|
| DE | 20 20 865 A1 | 11/1971 |
| DE | 27 15 209 A1 | 10/1978 |

(Continued)

OTHER PUBLICATIONS

International Search Report for PCT/EP2013/066063 mailed Nov. 12, 2013.

*Primary Examiner* — Sikarl Witherspoon
(74) *Attorney, Agent, or Firm* — Drinker Biddle & Reath LLP

(57) ABSTRACT

Supported noble metal-comprising catalysts which can be obtained by a1) application of a noble metal compound, optionally in admixture with additives acting as promoters, to a support material, then drying, and a2) application of a reducing agent to a support material, then drying, wherein steps a1) and a2) are repeated simultaneously or in alternating turns, or wherein either of the compounds is applied entirely and then the other one is applied entirely, b) optionally afterwards drying of the resulting product, and c) subsequent calcination, its use, especially for oxidative dehydrogenation and a process for producing it.

15 Claims, No Drawings

(56) References Cited

FOREIGN PATENT DOCUMENTS

| | | | |
|---|---|---|---|
| DE | 102008014910 A1 | 9/2009 | |
| EP | 244632 A2 | 11/1987 | |
| EP | 357292 A1 | 3/1990 | |
| EP | 619 142 A1 | 10/1994 | |
| EP | 0689872 A1 | 1/1996 | |
| EP | 0881206 A1 | 12/1998 | |
| GB | 941349 A | 11/1963 | |
| GB | 1338698 A | 11/1973 | |
| WO | WO-2011000668 A1 | 1/2011 | |

SUPPORTED NOBLE METAL-COMPRISING CATALYST FOR OXIDATIVE DEHYDROGENATION OR EPOXIDATION

CROSS-REFERENCE TO RELATED APPLICATIONS

This application is a national stage application (under 35 U.S.C. §371) of PCT/EP2013/066063, filed Jul. 31, 2013. This application claims priority to EP application 121778872.3 filed on Aug. 1, 2012 and to U.S. provisional application 61/678,143 filed on Aug. 1, 2012.

The entire disclosure of the prior applications is considered to be part of the disclosure of the instant application and is hereby incorporated by reference.

The present invention relates to a supported noble metal catalyst, a process for producing it and also its use for epoxidation or oxidative dehydrogenation, in particular for preparing olefinically unsaturated carbonyl compounds from olefinically unsaturated alcohols by oxidative dehydrogenation.

In particular, the present invention relates to the use of supported noble metal catalysts which can be obtained by a particular process for preparing 3-methylbut-2-en-1-al (MBA) from 3-methylbut-3-en-1-ol (MBE).

The preparation of alpha-beta-unsaturated carbonyl compounds by oxidative dehydrogenation over suitable catalysts is known to those skilled in the art and has been widely described in the literature.

Accordingly, DE-B-20 20 865 describes a process for preparing alpha-beta-unsaturated carbonyl compounds, in which, according to the description, alloys and metal compounds, especially some metal oxides of the transition elements can be used as dehydrogenation catalysts. Furthermore, this document states that the catalysts can be used in pure form or in the form of mixed catalysts with or without a support substance. Zinc oxide, cadmium oxide and manganese oxide and also mixed catalysts comprising the metals Cu, Ag and/or Zn are mentioned as being particularly suitable. No further information on the production of the catalyst is to be found in this document.

EP-A 881 206 describes a process for the continuous industrial preparation of unsaturated aliphatic aldehydes in a shell-and-tube reactor. Preferred catalysts for this process are said to be supported silver catalysts which comprise spheres of an inert support material coated with from 0.1 to 20% by weight, based on the amount of the support, of a layer of metallic silver in the form of a smooth, abrasion-resistant shell. Furthermore, a particular ratio of the largest diameter of the coated catalyst spheres to the internal diameter of the reaction tube should preferably be adhered to.

DE-A 27 15 209 discloses a process for preparing 3-alkylbuten-1-als, in which a catalyst having a total layer thickness of from 5 to 35 mm and 2 or more layers of silver and/or copper crystals is used. The production of the catalyst having a plurality of layers of the noble metal is relatively complicated.

EP-A 357 292 discloses a process for preparing ethylene oxide. Catalysts used in this process are silver catalysts in which the silver has been applied to a porous heat-resistant support having a particular specific surface area determined by the BET method. According to the information in this document, the silver can be applied as a suspension of silver or silver oxide in a liquid medium, for example water, to the support or by impregnation of the support with a solution of a silver compound. This silver compound is subsequently reduced to elemental silver by thermal treatment. This document gives no pointers to the possible use of the silver-comprising supported catalysts produced in this way for preparing ethylenically unsaturated carbonyl compounds.

EP-A 619 142 discloses silver catalysts for the oxidation of ethylene to ethylene oxide, which catalysts are obtained by impregnation with an aqueous (colloidal) solution of a silver salt followed by calcination.

Furthermore, the German patent application DE 10 2008 014 910 discloses noble metal-comprising catalysts which are obtained by application of a complexed sparingly soluble compound of a noble metal from suspension or solution to a support and subsequent thermal treatment.

From GB 941349 it is known to perform an ion exchange reaction with aluminosilicates thus replacing the major part of the ions with catalytically active metal ions and afterwards reducing those.

From Wang et al. "A Facile, Water-Based Synthesis of Highly Branched Nanostructures of Silver", *Langmuir* 2008, 24, 12042-12046 it is known to prepare highly branched nanostructures of silver at room temperature from an aqueous solution containing at the same time both ascorbic acid and silver nitrate. However, it is not disclosed that such structures could form on or in the presence of carrier/support substances nor is there any disclosure of the actual use as catalysts.

From WO 2011/000668 A1 supported noble metal-comprising catalysts which can be obtained by
a) application of colloidal noble metal in the form of a colloidal solution, optionally in admixture with additives acting as promoters, to a support material,
b1) drying of the resulting product at from 150 to 350° C., or
b2) drying of the resulting product at from 150 to 350° C. and subsequent calcination at from 350 to 550° C.
for epoxidation or oxidative dehydrogenation, a process for producing it, its use and also the use of colloidal noble metal for producing supported catalysts are known.

All documents cited in the present application are incorporated by reference in their entirety into the present disclosure.

3-Methylbut-2-en-1-al, also known under the trivial name prenal, is an important precursor for citral which is in turn an important starting material for many chemical syntheses. The catalysts described in the literature for preparing prenal (MBA, 3-methylbut-2-en-1-al) are produced by relatively complex processes and under production conditions which are overall in need of improvement. It would therefore be desirable to have noble metal-comprising supported catalysts for the synthesis of prenal from isoprenol (MBE, 3-methylbut-3-en-1-ol) which can be obtained in a simple way and whose selectivity can be controlled in a simple way by addition of compounds which act as promoters.

Furthermore, it would also be desirable to have catalysts for the preparation of ethylene oxide from ethylene which are simple to produce and give very good yields, conversions, selectivities, etc.

It was accordingly an object of the present invention to counter the disadvantages and requirements arising from the prior art and make available appropriate catalysts and production processes for these as well as uses.

According to the invention, this object is achieved by supported noble metal-comprising catalysts which are produced by
I) application of a noble metal compound, optionally in admixture with additives acting as promoters, to a support material in alternating turns with the application of a reducing agent to a support material with intermittent drying steps and subsequent thermal treatment of the product obtained, or
II) application of a noble metal compound, optionally in admixture with additives acting as promoters, and simultaneous application of a reducing agent to a support material with subsequent drying steps and subsequent thermal treatment of the product obtained, or III) application of the entire desired amount of a noble metal compound, optionally in admixture with additives acting as promoters, and subsequent application of the entire desired amount of a reducing agent to a support material, or vice versa, with intermittent drying step and subsequent thermal treatment of the product obtained.

The present invention further provides, in a further aspect to achieve the object, a process for producing this supported noble metal-comprising catalyst for epoxidation or oxidative dehydrogenation, in particular oxidative dehydrogenation.

The present invention likewise provides, in further aspect to achieve the object, for the use of the supported noble metal-comprising catalysts which are produced by the instant invention's process for epoxidation or oxidative dehydrogenation, in particular oxidative dehydrogenation, especially particularly for the preparation of olefinically unsaturated carbonyl compounds from olefinically unsaturated alcohols by oxidative dehydrogenation.

For the purposes of the present invention, all amounts are, unless indicated otherwise, by weight.

For the purposes of the present invention, the term "room temperature" refers to a temperature of 23° C. Temperatures indicated are, unless indicated otherwise, in degrees celsius (° C.).

Unless indicated otherwise, the reactions or process steps described are carried out at atmospheric pressure.

The term "thermal treatment" refers, for the purposes of the present invention, to i) calcination or (i.e. step c) of the instant invention's preparation), ii) drying and calcination (i.e. steps b) and c) of the instant invention's preparation).

Preferred embodiments of the invention may be found in the dependent claims and the following description and the examples.

The instant invention is based on a specific process of preparing a supported catalyst, comprising or consisting of the steps:

I-a1) application of a noble metal compound, optionally in admixture with additives acting as promoters, to a support material, then drying at from 60 to 200° C. for 10 to 180 seconds, and I-a2) application of a reducing agent to a support material, then drying at from 60 to 200° C. for 10 to 180 seconds, wherein steps I-a1) and I-a2) are repeated in alternating turns for 10 to 25 times, b) optionally afterwards drying of the resulting product at from 100 to 350° C. for 2 to 180 minutes, and c) subsequent calcination at from 350 to 550° C. for 15 minutes to 3 hours.

A first alternative process according to the instant invention differs form the above in the following steps, while the others are the same:

II-a) application of a noble metal compound, optionally in admixture with additives acting as promoters, to a support material, and at the same time application of a reducing agent to a support material, then drying at from 60 to 200° C. for 10 to 180 seconds, wherein step II-a) is repeated for 10 to 25 times.

A second alternative process according to the instant invention differs form the above in the following steps, while the others are the same:

III-a1) application of the entire desired amount of a noble metal compound, optionally in admixture with additives acting as promoters, to a support material, then drying at from 60 to 200° C. for 10 to 180 seconds, or III-a2) application of the entire desired amount of a reducing agent to a support material, then drying at from 60 to 200° C. for 10 to 180 seconds, and III-a3) application of the respective other compound.

Steps a1) and a2) together form an application cycle.

It is to be understood, that according to the instant invention the application cycle can start with either a1) or a2), i.e., the first material to be applied to the support material may be either the reducing agent or the noble metal compound.

Preference is given to the embodiment starting with a2).

From the specific preparation found in the context of the instant invention stem the instant invention's process, the instant invention's catalyst and the instant invention's use.

In the use according to the invention, a supported noble metal-comprising catalyst which can be obtained by the instant invention's process is used, i.e., according to the instant invention, a method for epoxidation or oxidative dehydrogenation of substrates, in particular oxidative dehydrogenation, is claimed, wherein the substrate(s) is (are) brought into contact with a catalyst prepared by the above mentioned steps a) to c) under conditions for epoxidation or oxidative dehydrogenation.

Preference is given in the instant invention to using salts of Cu, Au, Ag, Pd, Pt, Rh, Ru, W, Ir or Os or mixtures thereof as noble metal compounds.

Particular preference is given to using salts of Au and Ag or mixtures thereof as noble metal compounds.

Very particular preference is given to the use of silver salts.

The noble metal compounds in the context of the instant invention are ionic compounds, i.e., salts and are introduced into a solvent with which they will be applied to the catalyst support by adding them to the solvent and then stirring. This can preferably be carried out at room temperature and atmospheric pressure; however, it is likewise possible to adapt temperature and pressure to the respective requirements.

In one variant of the present invention, organic solvents, in particular $C_1$-$C_6$-alkanols, dimethyl sulphide, dimethyl sulphide, N-methylformamide, dimethylformamide, tetrahydrofuran, acetone, benzene, toluene, can be used.

In a further variant, it is possible to use water-miscible solvents, in particular preferably water-miscible solvents such as acetone, $C_1$-$C_6$-alkanols, dimethyl sulphide, dimethylformamide, tetrahydrofuran, N-methylformamide, in admixture with water as solvent.

For the purposes of the present invention, water is most preferably used as solvent for the noble metals.

In a preferred embodiment of the instant invention, the noble metals compounds are chosen from water soluble salts and employed in the form of their aqueous solutions.

One particularly preferred noble metal compound is silver nitrate, which is employed in the instant invention's preparation as its aqueous solution.

The noble metal salts are preferably present in solutions from which they are applied to the support material in proportions, calculated as noble metal based on the total solution, in the range from 5 to 35% by weight, preferably in the range from 10 to 30% by weight and particularly preferably in the range from 15 to 25% by weight.

Further additives suitable as promoters can be added to this solution of the noble metal compounds. Merely by way of example, mention may here be made of alkali metals, alkaline earth metals and transition metals (e.g. Li, Rb, Cs, Ca, Mg, V, Co, Ni, Ir or Re), which can be used, for example, as halides (fluorides, chlorides), carboxylates or nitrates or else in the form of sulphur-comprising anions such as sulphates, sulphites or sulphides. Phosphates, cyanides and hydroxides and also carbonates or mixtures thereof are likewise suitable. Finally, it is also possible to use anions of heteropolyacids, in particular heteropolyacids of the elements of transition groups six and seven of the Periodic Table (notation according to the IUPAC proposal of 1985). The above mentioned promoters can also be introduced separately from the solutions of the noble metal compounds. The way in which such promoters are used in supported catalyst systems are known per se to those skilled in the art and are described in the literature, so that further details are superfluous here.

In the instant invention any reducing agent can be used that is able to reduce the ions of the noble metal compounds as applied to the support.

Preferred reducing agents according to the instant invention are selected from the group consisting of hydrazine, hydroxylamine, formaldehyde, ascorbic acid, and mixtures thereof.

In another preferred embodiment, the reducing agents according to the instant invention are selected from the group consisting of hydrazine, hydroxylamine, formaldehyde, ascorbic acid, urea, and mixtures thereof.

The reducing agent is applied in the form of a solution to the support material.

Depending on the specific reducing agent employed the solution can be based on one or more organic solvents or be water-based, if necessary with an organic co-solvent.

As usable organic solvents those mentioned above may be employed.

The most preferred reducing agent according to the instant invention is ascorbic acid, which is preferably applied in the form of an aqueous solution.

Suitable support materials are known per se to those skilled in the art and are partly commercially available from for example, CeramTec, Saint-Gobain Norpro and are also described in the literature, to which reference is made here for further details.

Preferred support materials are steatite, aluminium oxides or aluminosilicates.

Particularly suitable supports are those which are present is spherical form, with the spherical support particles having an average diameter in the range from 0.5 to 3 mm.

According to the invention, preference is given to using support material in spherical form, with the spherical support particles having an average diameter in the range from 0.5 to 2.5 mm, for the reaction of MBE to form MBA, while the support materials preferably have the shape of hollow rings for epoxidation, in particular of ethylene. Preference is given to geometries of 5-10×5-10×2-5 mm, in particular 6×6×3 or 8×8×3 mm (external diameter times length times hole diameter of the hollow ring).

The precise size of the supports is nonetheless not critical for the present invention.

In a preferred embodiment of the present invention, the support materials for the reaction of MBE to form MBA have a very low porosity and have a BET surface area of not more than 1 m$^2$/g, preferably not more than 0.5 m$^2$/g, and in a particularly preferred embodiment comprise steatite.

In a preferred embodiment of the present invention, the support materials for epoxidation, in particular of ethylene, have a very low porosity and have a BET surface area of less than 10 m$^2$/g, preferably less than 3 m$^2$/g and particularly preferably less than 1 m$^2$/g, and, in a particularly preferred embodiment, comprise Al$_2$O$_3$.

The BET surface area of the supports which can be used according to the invention can be so low that it is down to 0.01 mm$^2$/g, or down to 0.001 m$^2$/g.

In some cases, hydrotalcites have been found to be suitable.

Hydrotalcite is generally understood to be a sheet material having the chemical formula $[M(II)_xM(III)_{1-x}(OH)_2]^{(1-x)+}[A_{1-x/n}]^{(1-x)-}*m\,H_2O$. Here, M(II) is a divalent metal, M(III) is a trivalent metal, A is an anion incorporated in the lattice, n is the valence of the anion, m is the number of incorporated water molecules and x is the molar ratio of M(II)/[M(II)+M(III)]. It is usual for x to be in the range from 0.2 to 0.33, which corresponds to molar ratios of M(III) to M(II) in the range from 2 to 4. As divalent metals, mention may here be made by way of example of Mg, Fe, Ni, Co, Zn and Mn, and as trivalent metals, mention may be made of Al, Ga, In, Co and Mn. The possible simultaneous presence of a plurality of divalent or trivalent metals in different molar ratios increases the structural variety of the suitable hydrotalcites.

As minerals of the hydrotalcite group, mention may here be made, purely by way of example, of manasseite, pyroaurite, sjögrenite, stichtite, barbertonite, desautelsite, meixnerite or takovite, which are described in the literature and whose compositions are known to those skilled in the art. A preferred hydrotalcite has the composition Mg$_6$Al$_2$(CO$_3$)(OH)$_{16}$*4 H$_2$O.

A further preferred support material is alpha-aluminium oxide.

A particularly preferred support material is steatite, a ceramic material based on natural raw materials which comprises the main component soapstone (Mg(Si$_4$O$_{10}$)(OH)$_2$), a natural magnesium silicate. Additions of clay and feldspar or barium carbonate can also be comprised.

The production of the noble metal-comprising catalysts according to the present invention comprises or consists of the following steps:

I-a1) application of a noble metal compound, optionally in admixture with additives acting as promoters, to a support material, then drying at from 60 to 200° C. for 10 to 180 seconds, and I-a2) application of a reducing agent to a support material, then drying at from 60 to 200° C. for 10 to 180 seconds, wherein steps I-a1) and I-a2) are repeated in alternating turns for 10 to 25 times, b) optionally afterwards drying of the resulting product at from 100 to 350° C. for 2 to 180 minutes, and c) subsequent calcination at from 350 to 550° C. for 15 minutes to 3 hours.

A first alternative production according to the instant invention differs form the above in the following steps, while the others are the same:

II-a) application of a noble metal compound, optionally in admixture with additives acting as promoters, to a support material, and at the same time application of a reducing agent to a support material, then drying at from 60 to 200° C. for 10 to 180 seconds, wherein step II-a) is repeated for 10 to 25 times.

A second alternative production according to the instant invention differs form the above in the following steps, while the others are the same:

III-a1) application of the entire desired amount of a noble metal compound, optionally in admixture with additives acting as promoters, to a support material, then drying at from 60 to 200° C. for 10 to 180 seconds, or III-a2) application of the entire desired amount of a reducing agent to a support material, then drying at from 60 to 200° C. for 10 to 180 seconds, and III-a3) application of the respective other compound.

Steps b) and c) will for the purposes of the present invention also be described by the collective term "thermal treatment".

Between steps b) and c), a delay time can be inserted. However, the duration of the delay time is not critical and is determined merely by the practical circumstances in each case. It is preferably in the range from 1 to 300 minutes.

In a variant of the present invention, it is possible to store the product after drying and calcine it only after any desired period of time (even after months); the catalyst performance is not impaired thereby.

In one variant of the present invention, it is possible to allow the steps b) and c) to go over into one another continuously.

This is a preferred embodiment.

In a variant of the present invention, the preparation does not comprise any further steps but consists of those mentioned.

This preparative process relates both to the noble metal-comprising catalysts of the invention and to the use according to the invention of the noble metal-comprising catalysts and of course to the process of the invention.

After the desired number of application cycles (steps a1) and a2)) in step b) the material prepared by alternating application of noble metal compound and reducing agent to a support material is optionally dried.

The number of application cycles depends on the desired characteristics of the catalyst. Usually from 1 to 200 application cycles are done, preferably 3 to 150 and especially 5 to 100. In one variant of the invention, 10 to 25 cycles can be used. These numbers, however, can be adapted to the specific needs.

Drying in step b) is preferably carried out for a time in the range from 2 to 180 minutes, preferably from 5 to 30 minutes and particularly preferably from 10 to 20 minutes.

The calcination in step c) is preferably carried out for a time in the range from 15 minutes to 3 hours, preferably from 30 minutes to 2 hours and particularly preferably from 40 to 90 minutes.

Drying in step b) is preferably carried out under conventional auxiliary conditions, i.e. at atmospheric pressure (or a low gauge pressure due to the apparatus—the introduction of gas into the apparatus leads to a small backpressure, generating the pressure in the apparatus) under a nitrogen, noble gas or air atmosphere, preferably air atmosphere and at temperatures of 100 to 350° C., preferably from 120 to 300° C. and particularly preferably from 200 to 285° C.

Calcination in step c) is preferably carried out under conventional conditions, i.e. at atmospheric pressure (or a low gauge pressure due to the apparatus—the introduction of gas into the apparatus leads to a small backpressure, generating the pressure in the apparatus) under a nitrogen, noble gas or air atmosphere, preferably air atmosphere and at temperatures of 350 to 550° C., preferably from 400 to 500° C. and particularly preferably from 425 to 475° C.

As a result of the employment of the reducing agent and the thermal treatment, a coating of noble metal itself is formed on the surface of the support material, including the internal surface area of the pores, from the noble metal compound and this noble metal coating then represents the active species of the supported catalyst.

The noble metal contents, measured in % by weight based on the catalyst (i.e. support plus noble metal), after the thermal treatment are generally in the range from 0.5 to 40% by weight, preferably in the range from 0.8 to 30% by weight and particularly preferably in the range from 1.3 to 20% by weight.

One variant of particularly preferred catalysts are those wherein the noble metal content based on the catalyst is between 1.2 and 2% by weight, in particular between 14 to 1.8% by weight. These catalysts are especially suitable for the preparation of MBA from MBE.

It has in some cases been found to be advantageous for different supports to have different contents of noble metal.

When the catalyst is to be used for oxidative dehydrogenation, in particular for preparing MBA from MBE, preference is given, according to the invention, to the noble metal contents being in the range from 0.5 to 6.0% by weight, in particular from 0.8 to 3% by weight, based on the catalyst.

When the catalyst is to be used for epoxidation, in particular for preparing ethylene oxide from ethylene, preference is given, according to the invention, to the noble metal contents being in the range from 5 to 40% by weight, in particular from 10 to 30% by weight, based on the catalyst.

When, in particular, steatite having a BET surface area of less than 1 $m^2/g$ is used as support material, the noble metal content, based on the catalyst, is preferably in the range from 0.5 to 2.5% by weight, particularly preferably in the range from 0.8 to 22% by weight and in particular in the range from 1.7 to 2.2% by weight.

When, in particular, alpha-aluminium oxide having a BET surface area of less than 10 $m^2/g$ is used as support material, the noble metal content, based on the catalyst, is preferably in the range from 5 to 40% by weight, particularly preferably in the range from 10 to 30% by weight and in particular in the range from 13 to 20% by weight.

A person skilled in the art can, on the basis of knowledge of the field, vary the precise content of the noble metal by means of simple measures such as noble metal content of the solution, number of application cycles and size and nature of the support and match them to the respective task.

For example, in the case of porous supports the water absorption into the pores of the support material can play a role and the impregnation solution can be tailored to the support, while in the case of nonporous supports the noble metal content can, inter alia, be controlled via the concentration and viscosity of the impregnation solution.

According to the invention, the supported noble metal-comprising catalysts which can be obtained by the above mentioned procedure can particularly advantageously be used for preparing 3-methylbut-2-en-1-al from 3-methylbut-3-en-1-ol. The product is also known by the trivial name prenal (MBA), and the starting material is known under the trivial name isoprenol (MBE).

In this particularly preferred use, the reaction is preferably carried out in a shell-and-tube reactor as described, for example, in EP-A 881 206 A1. For further details of the reactor geometry, explicit reference may be made here to EP-A 881 206 A1, page 2, lines 37 to 45 and page 5, lines 40 to 43, and EP-A 244 632 A2, FIGS. 1 to 3.

The use according to the invention of the noble metal-comprising supported catalysts which can be obtained as, described above makes it possible to obtain prenal from isoprenol in good yield and with good selectivity under mild temperature conditions. The reaction of isoprenol with the noble metal-comprising supported catalyst which can be obtained as described above forms a reaction mixture composed of 3-methylbut-3-en-1-al (IMBA) and 3-methylbut-2-en-1-al (MBA).

In the work-up of the reaction mixture, the desired reaction product is separated by distillation from unreacted starting material in a first stage. To be able to carry out this distillation in an economically advantageous way, it is advantageous to make use of an azeotrope which comprises 70% of 3-methylbut-3-en-1-al and 30% of 3-methylbut-2-en-1-al.

The use according to the invention of the supported noble metal-comprising catalyst which can be obtained as described above enables prenal to be prepared in good yield at low temperatures and with good selectivity from isoprenol.

Within the framework of the present invention, it is possible, for example, to achieve yields of greater than 45%, in particular 47% and more, and selectivities of greater than 85%, in particular 90% and more, in, for example, the reaction of MBE to form MBA at temperatures of from 320 to 400° C., preferably of from 340 to 385° C.

In a further variant, the supported noble metal-comprising catalysts which can be obtained by the above procedure can, according to the invention, be used for the preparation of ethylene oxide from ethylene.

Of course, the catalysts of the invention can also be used for reactions other than those mentioned, in particular for oxidations in general.

Accordingly, the present invention also comprises the use in general of the catalysts of the invention for oxidation reactions.

An advantage of the present invention is accordingly that the production of the catalysts can be controlled (varied) very simply and well. A further advantage is that very good yields and selectivities are achieved by means of the catalysts of the invention.

A further advantage of the present invention is that catalysts which even when the amount of gas is increased significantly by 10 or even 20% display no deterioration in performance but give a constant selectivity and conversion are obtained.

In a less preferred but possible variant of the present invention, epoxidation and oxidative dehydrogenation can be carried out simultaneously.

It is of course possible to use the catalysts of the invention both in processes which are carried out in a single pass and also in processes carried out in the recycle mode.

The various embodiments of the present invention, e.g. those of various dependent claims, can be combined with one another in anyway.

The invention will now be illustrated with reference to the following non-limiting examples.

EXAMPLES

Example 1

Catalyst Preparation 50 g of steatite spheres (average particle size 1.8-2.2 mm) were inserted into a coating device with driving motor from Erweka AR 401 and small granuling drum (diameter d=15 cm) and rotated at about 125 turns per minute.

Then a puff of ascorbic acid solution (obtained from Fluka, 99.5%; 60 g solved in 200 ml water (=300 g/l)) is applied to the steatite spheres with the aid of the hand dispenser from Desaga.

In order to dry the spheres, the air flow of a hot air drier set at full power was directed to the granuling drum.

After drying for 30 seconds until the product isn't sticky anymore, a puff of a silver nitrate solution ($AgNO_3$ obtained from Riedel de Haen, 99.8-100.5%; 27.8 g solved in 15 ml water) was applied to the spheres with another hand dispenser and dried for about 30 seconds.

The application of the ascorbic acid solution and of the silver nitrate solution was done in alternating turns for 18 times.

After ten application turns, the rotation speed of the granuling drum was set to 175 turns per minute.

The resulting spheres were evenly coloured dark-grey to black.

In sum, 3.56 g of silver nitrate solution (=2.31 g $AgNO_3$) and 1.71 g of ascorbic acid solution were used.

Next, the spheres were dried for 2 hours in a drying oven at 120° C. to remove water, after which homogeneously coated dark-grey spheres were obtained.

Finally, calcination was performed with a temperature increasing rate of about 1.4 Kelvin per minute to 450° C. and kept at that temperature for one hour under ambient air conditions.

50.85 g of product in the form of pale coloured spheres were obtained (0.85 g mass applied=1.67%)

The elemental analysis of the catalysts showed 1.7% per weight, based on the entire catalyst, of silver.

Example 2

Preparation of Prenal with the Catalyst as Prepared in Example 1

A bed of 10 ml undiluted catalyst produced as per example 1 was introduced into a quartz reactor. The reaction, (preparation of 3-methylbut-2-en-1-al from 3-methylbut-3-en-1-ol) was then carried out by vaporizing 110 g/h of MBE and 50 l/h of air by means of a thin film evaporator, with the temperature being set so that the MBE conversion was 55% (355° C. over an electrical stove were employed).

At 55% conversion 87 mol % selectivity were reached (MBA+iMBA), 5.5% butene.

Example 3

Catalyst Preparation 50 g of steatite spheres (average particle size 1.8-2.2 mm) were inserted into a coating device with driving motor from Erweka AR 401 and small granuling drum (diameter d=15 cm) and rotated at about 125 turns per minute.

Then a puff of ascorbic acid solution (obtained from Fluka, 99.5%; 60 g solved in 200 ml water (=300 g/l)) and a puff of a silver nitrate solution ($AgNO_3$ obtained from Riedel de Haen, 99.8-100.5%; 27.8 g solved in 15 ml water) were simultaneously applied to the steatite spheres with the aid of hand dispensers from Desaga.

In order to dry the spheres, the air flow of a hot air drier set at medium power was directed to the granuling drum and the product was dried for about 2 minutes.

The simultaneous application of the ascorbic acid solution and of the silver nitrate solution was done 21 times.

After five of those application turns, the rotation speed of the granuling drum was set to 175 turns per minute.

The resulting spheres were evenly coloured dark-grey to black.

In sum, 3.62 g of silver nitrate solution (=2.35 g $AgNO_3$) and 1.91 g of ascorbic acid solution were used.

Next, the spheres were dried for 2 hours in a drying oven at 120° C. to remove water, after which 51.30 g (1.30 g mass applied=2.53%) of homogeneously coated dark-grey spheres were obtained.

Finally, calcination was performed with a temperature increasing rate of about 1.4 Kelvin per minute to 450° C. and kept at that temperature for one hour under ambient air conditions.

50.83 g of product in the form of pale coloured spheres were obtained (0.83 g mass applied=1.63%)

The elemental analysis of the catalysts showed 1.7% per weight, based on the entire catalyst, of silver.

Example 4

Preparation of Prenal with the Catalyst as Prepared in Example 3

The procedure of example 2 was followed with the catalyst of example 3.

At 55% MBA conversion (360° C. employed) 85 mol % selectivity were reached.

Results:

The catalyst prepared as per example 1 is significantly superior to the conventional catalyst by means of which yields of only 45% can be achieved and to the catalyst described in WO 2011/000668 A1, which showed only a selectivity of 85% under the same conditions.

The catalyst prepared as per example 3 is also significantly superior to the conventional catalyst and at least equal to the catalyst described in WO 2011/000668 A1.

The invention claimed is:

1. A process comprising utilizing a supported noble metal-comprising catalyst prepared by
    I-a1) application of a noble metal compound, optionally in admixture with additives acting as promoters, to a support material, then drying at from 60 to 200° C. for 10 to 180 seconds,
    and
    I-a2) application of a reducing agent to a support material, then drying at from 60 to 200° C. for 10 to 180 seconds,
    wherein steps I-a1) and I-a2) are repeated in alternating turns for 10 to 25 times,
    or
    II-a) application of a noble metal compound, optionally in admixture with additives acting as promoters, and at the same time of a reducing agent to a support material, then drying at from 60 to 200° C. for 10 to 180 seconds,
    wherein step II-a) is repeated for 10 to 25 times,
    or
    III-a2) application of the entire desired amount of a reducing agent to a support material, then drying at from 60 to 200° C. for 10 to 180 seconds, and
    III-a3) application of the respective other compound,
    b) optionally afterwards drying of the resulting product at from 100 to 350° C. for 2 to 180 minutes, and
    c) subsequent calcination at from 350 to 550° C. for 15 minutes to 3 hours,
    in an epoxidation or oxidative dehydrogenation.

2. The process according to claim 1 for oxidative dehydrogenation.

3. The process according to claim 1 for preparing olefinically unsaturated carbonyl compounds from olefinically unsaturated alcohols by oxidative dehydrogenation.

4. The process according claim 1, wherein a noble metal compound selected from the group consisting of salts of Cu, Au, Ag, Pd, Pt, Rh, Ru, W, Os and mixtures thereof is used as noble metal compound.

5. The process according to claim 1, wherein the reducing agent is selected from the group consisting of hydrazine, hydroxylamine, formaldehyde, ascorbic acid, urea, and mixtures thereof.

6. The process according to claim 1, wherein the reducing agent is ascorbic acid, in the form of an aqueous solution.

7. The process according to claim 1, wherein 3-methylbut-2-en-1-al and 3-methylbut-3-en-1-al are prepared from 3-methylbut-3-en-1-ol.

8. A process for producing a supported noble metal-comprising catalyst for epoxidation or oxidative dehydrogenation, comprising
    I-a1) applying a noble metal compound, optionally in admixture with additives acting as promoters, to a support material, then drying at from 60 to 200° C. for 10 to 180 seconds,
    and
    I-a2) applying a reducing agent to a support material, then drying at from 60 to 200° C. for 10 to 180 seconds,
    wherein steps I-a1) and I-a2) are repeated in alternating turns for 10 to 25 times,
    or
    II-a) applying a noble metal compound, optionally in admixture with additives acting as promoters, and at the same time of a reducing agent to a support material, then drying at from 60 to 200° C. for 10 to 180 seconds,
    wherein step II-a) is repeated for 10 to 25 times,
    or
    III-a2) applying the entire desired amount of a reducing agent to a support material, then drying at from 60 to 200° C. for 10 to 180 seconds, and
    III-a3) applying the respective other compound,
    b) optionally afterwards drying the resulting product from 100 to 350° C. for 2 to 180 minutes, and
    c) subsequently calcinining at from 350 to 550° C. for 15 minutes to 3 hours.

9. The process according to claim 8, wherein a supported noble metal-comprising catalyst for the oxidative dehydrogenation of olefinically unsaturated alcohols is produced.

10. The process according to claim 8, wherein a noble metal compound selected from the group consisting of salts of Cu, Au, Ag, Pd, Pt, Rh, Ru, W, Os and mixtures thereof is used as noble metal compound.

11. The process according to claim 8, wherein a basic or acidic support material is used as support material.

12. The process according to claim 11, wherein a support material selected from the group consisting of steatite, aluminium oxide, aluminosilicates and mixtures thereof is used as support material.

13. The process according to claim 8, wherein the reducing agent is selected from the group consisting of hydrazine, hydroxylamine, formaldehyde, ascorbic acid, urea, and mixtures thereof.

14. A supported noble metal-comprising catalyst prepared by
    I-a1) applying a noble metal compound, wherein the noble metal compound is selected from the group consisting of salts of Cu, Au, Ag, Pd, Pt, Rh, Ru, W, Os and mixtures thereof, optionally in admixture with additives acting as promoters, to a support material, then drying at from 60 to 200° C. for 10 to 180 seconds, and I-a2) applying a reducing agent, wherein the reducing agent is selected from the group consisting of hydrazine, hydroxylamine, formaldehyde, urea, ascorbic acid, and mixtures thereof, to a support material, then drying at from 60 to 200° C. for 10 to 180 seconds, wherein steps I-a1) and I-a2) are repeated in alternating turns for 10 to 25 times, or II-a) applying a noble metal compound, wherein the noble metal compound is selected from the group consisting of salts of Cu, Au, Ag, Pd, Pt, Rh, Ru, W, Os and mixtures thereof, optionally in admixture with additives acting as promoters, and at the same time of a reducing agent, wherein the reducing agent is selected from the group consisting of hydrazine, hydroxylamine, formaldehyde, urea, ascorbic acid, and mixtures thereof, to a support material, then drying at from 60 to 200° C. for 10 to 180 seconds, wherein step II-a) is repeated for 10 to 25 times, or III-a2) applying the entire desired amount of a reducing agent, wherein the reducing agent is selected from the group consisting of hydrazine, hydroxylamine, formaldehyde, urea, ascorbic acid, and mixtures thereof, to a support material, then drying at from 60 to 200° C. for 10 to 180 seconds, and III-a3) applying the respective other compound, b) optionally afterwards drying of the resulting product at from 100 to 350° C. for 2 to 180 minutes, and c) subsequent calcination at from 350 to 550° C. for 15 minutes to 3 hours.

15. The catalyst according to claim 14, wherein a support material selected from the group consisting of steatite, aluminium oxide, aluminosilicates and mixtures thereof is used as support material.

* * * * *